US012751980B2

(12) United States Patent
Mao et al.

(10) Patent No.: US 12,751,980 B2
(45) Date of Patent: Oct. 6, 2026

(54) ***Bifidobacterium longum* CCFM1206 CAPABLE OF PRODUCING SULFORAPHANE AND RELIEVING INFLAMMATION**

(71) Applicant: Jiangnan University, Wuxi (CN)

(72) Inventors: Bingyong Mao, Wuxi (CN); Jiaying Wu, Wuxi (CN); Shumao Cui, Wuxi (CN); Xin Tang, Wuxi (CN); Qiuxiang Zhang, Wuxi (CN); Jianxin Zhao, Wuxi (CN); Wei Chen, Wuxi (CN)

(73) Assignee: Jiangnan University, Wuxi (CN)

( * ) Notice: Subject to any disclaimer, the term of this patent is extended or adjusted under 35 U.S.C. 154(b) by 150 days.

(21) Appl. No.: 18/780,491

(22) Filed: Jul. 23, 2024

(65) Prior Publication Data

US 2024/0374660 A1 Nov. 14, 2024

Related U.S. Application Data

(63) Continuation of application No. PCT/CN2023/085418, filed on Mar. 31, 2023.

(30) Foreign Application Priority Data

Apr. 18, 2022 (CN) ......................... 202210404726.6

(51) Int. Cl.
*A61K 35/745* (2015.01)
*A61K 31/7028* (2006.01)
(Continued)

(52) U.S. Cl.
CPC ........ *A61K 35/745* (2013.01); *A61K 31/7028* (2013.01); *A61K 36/31* (2013.01); *A61P 1/04* (2018.01); *A61P 29/00* (2018.01)

(58) Field of Classification Search
None
See application file for complete search history.

(56) References Cited

U.S. PATENT DOCUMENTS

2016/0279090 A1 9/2016 Kosi-Kupe

FOREIGN PATENT DOCUMENTS

CN 111419857 A 7/2020
CN 114657105 A 6/2022

OTHER PUBLICATIONS

Shunyu Yao et al., "Bifidobacterium Longum: Protection against Inflammatory Bowel Disease", J Immunol Res .Jul. 23, 2021.

(Continued)

*Primary Examiner* — David W Berke-Schlessel
(74) *Attorney, Agent, or Firm* — IPro, PLLC; Na Xu

(57) ABSTRACT

The present disclosure relates to a *Bifidobacterium longum* CCFM1206 capable of producing sulforaphane and relieving inflammation, and belongs to the field of microbial technology. *B. longum* CCFM1206 provided by the present disclosure can convert glucoraphanin to sulforaphane, promoting the metabolism of glucoraphanin and the generation of sulforaphane in mammals. The *B. longum* CCFM1206 according to the present disclosure can be used alone or in combination with glucoraphanin to relieve weight loss during ulcerative colitis, reduce the release of pro-inflammatory factors from the colon, improve the colonic barrier function, relieve the splenomegaly due to systemic inflammation, reduce the levels of pro-inflammatory factors in the serum, reduce the levels of pro-inflammatory factors in the liver tissues and increase the levels of anti-inflammatory factors, and increase the levels of short-chain fatty acids.

11 Claims, 12 Drawing Sheets

Specification includes a Sequence Listing.

(51) Int. Cl.
*A61K 36/31* (2006.01)
*A61P 1/04* (2006.01)
*A61P 29/00* (2006.01)

(56) References Cited

OTHER PUBLICATIONS

Mei Dai et al. "Research progress on the glucosinolates in broccoli" Food Research and development, V 38(6) Mar. 20, 2017.

*Bifidobacterium longum* CCFM1206 CAPABLE OF PRODUCING SULFORAPHANE AND RELIEVING INFLAMMATION

REFERENCE TO SEQUENCE LISTING

The instant application contains a Sequence Listing in XML format as a file named "3050-YGHY-2023-46.xml", created on Aug. 13 2026, of 8238 bytes in size, and which is hereby incorporated by reference in its entirety.

TECHNICAL FIELD

The present disclosure relates to a *B. longum* CCFM1206 capable of producing sulforaphane and relieving inflammation, and belongs to the field of microbial technology.

BACKGROUND

Sulforaphane, with the molecular formula $C_6H_{11}NOS_2$, is an isothiocyanate that is a secondary metabolite of thioglucoside (primarily glucoraphanin) found in cruciferous plants. However, the sulforaphane is not normally found in natural plants, but is stably found in the plant in the form of its precursor glucoraphanin. Only when the plant tissue is damaged does the hydrolysis of glucoraphanin with myrosinase result in the production of sulforaphane. The hydrolysis process is affected by a variety of factors such as pH, temperature, and moisture, which can lead to a decrease in yield. In addition, sulforaphane is unstable and extremely volatile, making it difficult to extract sulforaphane from natural plants.

Cruciferous vegetables such as broccoli, cabbage, and kale have been reported to be rich in glucoraphanin. However, after cooking treatments such as boiling and stir-frying, the plant-derived myrosinase will be inactivated due to heat and will no longer have the ability to hydrolyze glucoraphanin. Although the human intestinal microbiota also has the ability to convert glucoraphanin into sulforaphane, there are individual differences in the conversion of glucoraphanin. The results of a population-based experiment showed that the conversion rates of glucoraphanin in volunteers ranged from 1.1% to 40%, but the average conversion rate was only 10.4%-11.8%. Therefore, improving the metabolism of glucoraphanin by intestinal microbiota is conducive to the absorption and efficacy of sulforaphane.

Inflammation is often the cause of many diseases, and Sturm and Wagner have directly linked inflammatory states to the risk of cancer development. The sulforaphane is among the isothiocyanates with the most potent chemopreventive effect on inflammation and good anti-inflammatory properties. Studies have shown that the sulforaphane is an inducer of nuclear factor (erythroid-derived 2)-like 2 (Nrf2), which exerts antioxidant effects by upregulating antioxidant enzymes, such as quinone oxidoreductase-1 (NQO1) and superoxide dismutase (SOD), through activation of the Nrf2 signaling pathway. In addition, sulforaphane can inhibit the binding of redox-sensitive DNA and the trans-activation of NF-κB by interacting with sulfhydryl groups through the formation of dithiocarbamate, thus suppressing the inflammatory response.

Currently, there are no bacterial strains capable of effectively converting glucoraphanin to sulforaphane with full anti-inflammatory activity. Therefore, it is desirable to screen for a strain capable of bioconverting and producing sulforaphane and that the synergistic effect of sulforaphane and the strain is superior to the effect when they are present alone.

SUMMARY

The technical problem to be solved by the present disclosure is to provide a strain of *B. longum* CCFM1206 capable of producing sulforaphane and to prevent and relive inflammation with *B. longum* CCFM1206 alone or in combination with glucoraphanin (or a composition containing glucoraphanin).

The present disclosure provides a *B. longum* CCFM1206, which was deposited at Guangdong Microbial Culture Collection Center on Dec. 15, 2021, with a deposit number of GDMCC NO: 62129.

The *B. longum* CCFM1206 has the following characteristics:

(1) morphological characteristics: the shape of the bacterium is irregular, curved, "V"-shaped or "Y"-shaped with different sizes at both ends; and (2) colony characteristics: after 24-48 h culture on MRS solid plate, the colony is smooth, round, milky white or white opaque, and the colony diameter is 0.5-1 mm.

The present disclosure also provides a probiotic preparation including the *B. longum* CCFM1206.

In one embodiment, the *B. longum* CCFM1206 is present in the probiotic preparation in a level of $\geq 1\times10^6$ CFU/g or $1\times10^6$ CFU/mL.

In one embodiment, the probiotic preparation further contains glucoraphanin.

In one embodiment, the probiotic preparation further contains a broccoli seed aqueous extract, where the level of glucoraphanin is ≥40 mg/g.

In one embodiment, the probiotic preparation is a lyophilized powder prepared from a bacterial solution of the *B. longum* CCFM1206, where the active *B. longum* CCFM1206 is present in a level of $1.0\times10^6$ cfu/g or more.

In one embodiment, the probiotic preparation is prepared by inoculating the *B. longum* CCFM1206 at an inoculum size of 2%-4% into an MRS medium, anaerobically incubating at 37° C. for 24 h, and centrifuging to collect the bacterium, which is rinsed with a phosphate buffer at pH 7.0-7.2 for 2-4 times and resuspended with a protective agent to reach a concentration of $10^{10}$ cfu/mL; then incubating the suspension at 37° C. under an anaerobic condition for 1 h and lyophilizing to obtain the probiotic preparation.

In one embodiment, the protective agent contains 100 g/L skimmed milk powder, 30 ml/L glycerol, 100 g/L maltodextrin, 150 g/L trehalose, and 10 g/L sodium L-glutamate.

The present disclosure also provides a method for obtaining sulforaphane by biotransforming, including inoculating *B. longum* CCFM1206 into a fermentation medium and incubating for at least 24 h, where glucoraphanin is used as a carbon source in the fermentation medium.

In one embodiment, the fermentation medium contains: 10 g/L peptone, 10 g/L beef extract, 10 g/L broccoli seed aqueous extract, 2 g/L anhydrous sodium acetate, 5 g/L yeast powder, 2 g/L diammonium hydrogen citrate, 2.6 g/L $K_2HPO_4\cdot3H_2O$, 0.1 g/L $MgSO_4\cdot7H_2O$, 0.05 g/L $MnSO_4$, 1 ml/L Tween 80, and 0.5 g/L cysteine hydrochloride at pH=6.8.

In one embodiment, the level of the broccoli seed aqueous extract is 10 g/L.

The present disclosure also provides a method for preventing and/or ameliorating the symptoms of ulcerative colitis (UC) and/or systemic inflammation, including using the *B. longum* CCFM1206 alone or in combination with glucoraphanin as a medication.

In one embodiment, the medication further includes a pharmaceutically acceptable excipient; the pharmaceutically acceptable excipient means any diluent, adjuvant and/or carrier that can be used in the pharmaceutical field.

The present disclosure also provides a food product, nutraceutical, dietary supplement or medication containing the *B. longum* CCFM1206.

In one embodiment, *B. longum* CCFM1206 is present in the food product, nutraceutical and dietary supplement in a level of not less than $1.0\times10^6$ CFU/ml or $1.0\times10^6$ CFU/g.

In one embodiment, the food product, nutraceutical and dietary supplement further contains a composition containing glucoraphanin.

In one embodiment, the composition containing glucoraphanin means a vegetable or vegetable extract containing glucoraphanin; the vegetable includes, but is not limited to, one or a mixture of more than one of broccoli, cabbage, kale, and mustard.

In one embodiment, the fermented food product includes a fermented cow's milk and milk beverage as well as a fermented fruit and vegetable product; the fruit and vegetable product includes a juice beverage, a fruit and vegetable puree, and a kimchi made from broccoli, cabbage, and the like.

In one embodiment, the amelioration of the symptoms of ulcerative colitis includes, but is not limited to, the following:

(1) reducing the weight loss due to ulcerative colitis;
(2) relieving the shortening of colon length;
(3) reducing the levels of pro-inflammatory factors in colon; and
(4) regulating the transcriptional levels of tight junction proteins in colon and improving the colonic barrier function.

In one embodiment, the pro-inflammatory factors in colon include TNF-α, IL-6 and IL-1β.

In one embodiment, the tight junction proteins in colon include Claudin-1, Occudin and ZO-1.

In one embodiment, the amelioration of the symptoms of LPS-induced systemic inflammation includes, but is not limited to, the following:

(1) relieving the splenomegaly due to inflammation;
(2) reducing the levels of pro-inflammatory factors in serum;
(3) reducing the levels of pro-inflammatory factors and increasing the levels of anti-inflammatory factors in liver tissue; and
(4) increasing the levels of short-chain fatty acids in the intestines.

In one embodiment, the pro-inflammatory factors in serum include TNF-α, IL-6 and IL-1β.

In one embodiment, the pro-inflammatory factors in liver include TNF-α and IL-6 and the anti-inflammatory factor in liver includes IL-10.

In one embodiment, the short-chain fatty acids include acetic acid, propionic acid, and butyric acid.

Beneficial Effects (1) the present disclosure screens for a *B. longum* CCFM1206 with enzyme activity for sulforaphane, which can convert glucoraphanin to sulforaphane, where this *B. longum* CCFM1206 is inoculated into a modified MRS medium and fermented for 24 h, and 16.76 μM sulforaphane are detected in the fermentation broth;
(2) the *B. longum* CCFM1206 according to the present disclosure can significantly promote the metabolism of glucoraphanin and the generation of sulforaphane in mammals, where the ingestion of *B. longum* CCFM1206 results in 1.5 to 1.7 times the level of sulforaphane in the body than would be the case in the absence of ingestion;
(3) the present disclosure provides a use of *B. longum* CCFM1206 alone or in combination with a glucoraphanin-containing diet composition for relieving the weight loss during ulcerative colitis, reducing the release of pro-inflammatory factors from colon, and improving the colonic barrier function; and
(4) the present disclosure provides a *B. longum* CCFM1206 and a glucoraphanin-containing diet composition capable of relieving the splenomegaly due to LPS-induced systemic inflammation, reducing the levels of pro-inflammatory factors in serum, reducing the levels of pro-inflammatory factors and increasing the levels of anti-inflammatory factors in liver tissue, and increasing the levels of short-chain fatty acids.

Deposit of Biological Materials

A *B. longum* CCFM1206 having the taxonomic name of *B. longum* was deposited at Guangdong Microbial Culture Collection Center on Dec. 15, 2021 with a deposit number of GDMCC NO: 62129, and the deposit address is 5th Floor, Building 59, No. 100, Xianlie Middle Road, Guangzhou.

DETAILED DESCRIPTION

Figure 1:
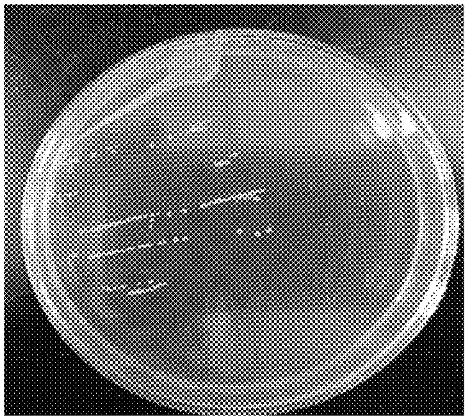
FIG. 1 is a graph showing the colony morphology of *B. longum* CCFM1206.

The 6-week-old SPF male C57BL/6J mice involved in the following examples were purchased from Vital River Laboratory Animal Technology Co., Ltd. The dextran sulfate sodium salt (DSS) and lipopolysaccharide (LPS) involved in the following examples were purchased from Sigma in Shanghai. The broccoli seed aqueous extract was purchased from Ganzhou Huahan Biotechnology Co., Ltd. and the level of glucoraphanin per gram of broccoli seed aqueous extract was 20% by mass. The ELISA kit involved in the following examples was purchased from Shanghai Enzyme-linked Biotechnology Co., Ltd. Other reagents involved in the following examples were purchased from Sinopharm Chemical Reagent Co., Ltd.

The Medium Involved in the Following Examples are as Follows:

MRS solid medium: 10 g/L peptone, 10 g/L beef extract, 20 g/L glucose, 2 g/L sodium acetate, 5 g/L yeast powder, 2 g/L diammonium hydrogen citrate, 2.6 g/L $K_2HPO_4 \cdot 3H_2O$, 0.1 g/L $MgSO_4 \cdot 7H_2O$, 0.05 g/L $MnSO_4$, 1 mL/L Tween 80, 20 g/L agar, and 0.5 g/L cysteine hydrochloride.

MRS liquid medium: 10 g/L peptone, 10 g/L beef extract, 20 g/L glucose, 2 g/L sodium acetate, 5 g/L yeast powder, 2 g/L diammonium hydrogen citrate, 2.6 g/L $K_2HPO_4 \cdot 3H_2O$, 0.1 g/L $MgSO_4 \cdot 7H_2O$, 0.05 g/L $MnSO_4$, 1 mL/L Tween 80, and 0.5 g/L cysteine hydrochloride.

Modified MRS solid medium: 10 g/L peptone, 10 g/L beef extract, 10 g/L broccoli seed aqueous extract, 2 g/L anhydrous sodium acetate, 5 g/L yeast powder, 2 g/L diammonium hydrogen citrate, 2.6 g/L $K_2HPO_4 \cdot 3H_2O$, 0.1 g/L $MgSO_4 \cdot 7H_2O$, 0.05 g/L $MnSO_4$, 1 ml/L Tween 80, 20 g/L agar, and 0.5 g/L cysteine hydrochloride.

Modified MRS liquid medium: 10 g/L peptone, 10 g/L beef extract, 10 g/L broccoli seed aqueous extract, 2 g/L anhydrous sodium acetate, 5 g/L yeast powder, 2 g/L diammonium hydrogen citrate, 2.6 g/L $K_2HPO_4 \cdot 3H_2O$, 0.1 g/L $MgSO_4 \cdot 7H_2O$, 0.05 g/L $MnSO_4$, 1 ml/L Tween 80, and 0.5 g/L cysteine hydrochloride.

The Detection Methods Involved in the Following Examples are as Follows:

Detection method of sulforaphane: qualitative and quantitative analyses were performed using UPLC-Q Exactive quadrupole-electrostatic field orbit trap high-resolution mass spectrometer (Thermo Fisher Scientific, Inc., USA) by parallel-reaction-monitoring (PRM). The chromatographic column was a Waters HSS T3 column (1.8 μm×2.1 mm×100 mm); the column temperature was 35° C.; the mobile phases were as follows: A-0.1% formic acid in water and B-acetonitrile; the flow rate was 0.3 mL/min; the injection volume was 2 μL; and the gradient elution was as follows: 0-3.0 min 5% B, 3-9 min 5%-30% B, 9-15 min 30%-100% B, 15-16 min 100% B, 16-16.5 min 100%-5% B, and 16.5-20 min 5% B. The ion source was a HESI source (heated ESI); the spray voltages were 3.5 kV (+) and 3.2 kV (−); the sheath gas volumetric flow rate was 35 μl min-1; the ion transfer tube temperature was 320° C.; the auxiliary gas flow rate was 15 μL-min 1; and the auxiliary gas temperature was 320° C. The scanning mode was PRM (100-500 m/z); the resolution was 35000; the acquisition polarity was positive; the AGC target was 5e 5; and the Maximum IT was 100 ms.

Determination of short-chain fatty acid level: Trace 1300 GC-MS (Thermo Fisher Scientific, Inc., USA) was used for the determination. The chromatographic column was a Rtx Wax column (30 m long, 25 μm inner diameter); the carrier gas was helium at a flow rate of 2 mL/min; the injection volume was 1 μl, and the sample was heated up to 140° C. at 7.5° C./min, and then heated up to 200° C. at 60° C./min for 3 min, with the ionization temperature of 20° C. The analysis was carried out in a full scan mode in order to make a standard curve by external standardization, thus calculating the concentration of each short-chain fatty acid.

Example 1: Screening, Characterization, Observation and Deposit of *B. longum* CCFM1206

1. Screening 0.5 g of fresh fecal sample from a healthy adult was added to a 4.5 mL of 0.9% normal saline for gradient dilution, an appropriate gradient dilution was selected and plated in a modified MRS solid medium with 0.2% bromocresol violet, and incubated under an anaerobic condition at 37° C. for 24-48 h. A single colony whose discoloration circle turned yellow obviously was selected and inoculated onto MRS plates for streaking purification. The single colony was picked and transferred to an MRS liquid medium for bacterial enrichment and preserved in 30% glycerol to obtain a strain of *B. longum* CCFM1206.

2. Identification

The whole genomic DNA of strain CCFM1206 was extracted for 16S rDNA amplification, and the amplified DNA fragments were collected for sequencing. The sequencing was accomplished by Suzhou GENEWIZ Biotechnology Co., Ltd. The sequence was subjected to a nucleic acid sequence alignment in NCBI, which showed that the strain was *B. longum* and was named as *B. longum* CCFM1206.

3. Observation

The bacterial solution of *B. longum* CCFM1206 was picked through dipping and streaked on an MRS solid medium, and anaerobically incubated at 37° C. for 48 h. After which, the colonies were observed and found to be round, white and smooth (FIG. 1).

4. Preservation

The single colony of *B. longum* CCFM1206 was picked and inoculated into an MRS liquid medium, and anaerobically incubated at 37° C. for 24 h to obtain the bacterial solution. 1 mL of bacterial solution was charged in a sterile centrifuge tube and centrifuged at 8000 r/min for 3 min, then the upper layer of medium was discarded, and the bacterial sludge was resuspended into a 30% glycerol solution and preserved at −80° C.

Example 2: Fermentation by *B. longum* CCFM1206 for the Production of Sulforaphane

*B. longum* CCFM1206 preserved at −80° C. was streaked in an MRS solid medium, anaerobically incubated at 37° C. for 24-48 h, passaged with an MRS liquid medium for 2-3 times, then inoculated into a modified MRS liquid medium at an inoculum size of 2%-4% and anaerobically incubated at 37° C. for 24 h. The fermentation broth obtained was used for determining the sulforaphane level.

Figure 2:
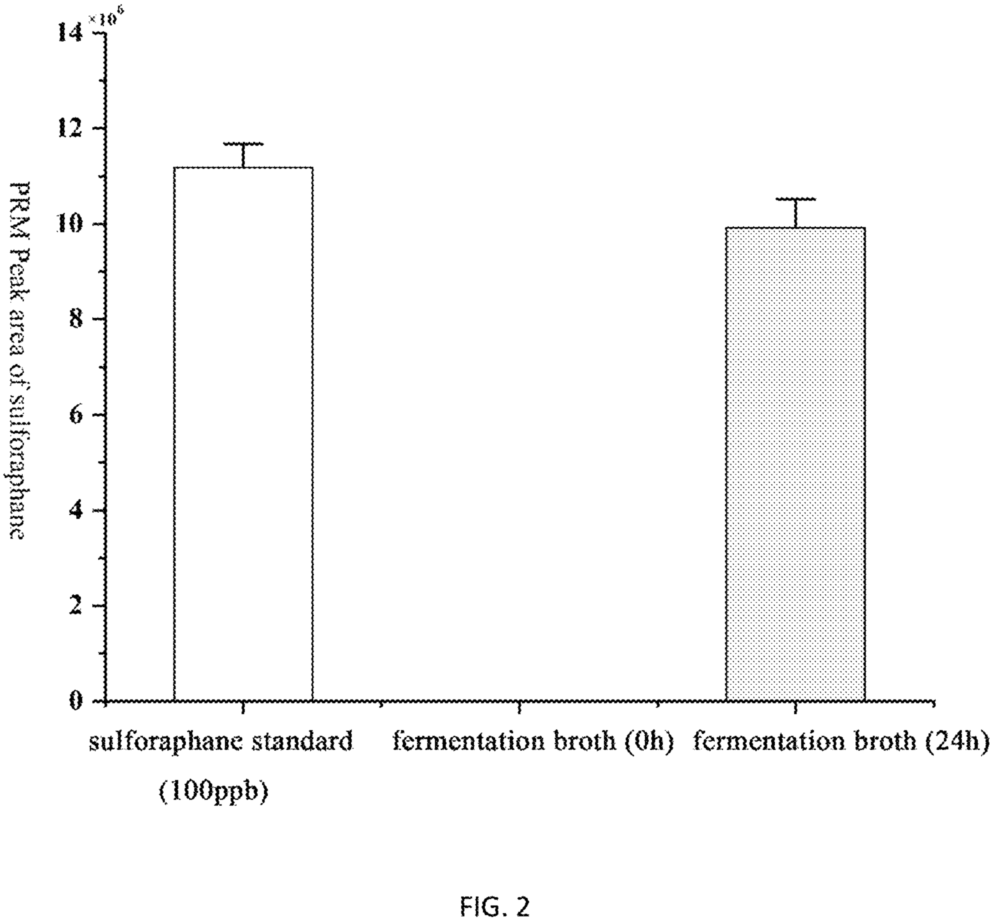
FIG. 2 is a graph showing the result of the detection of sulforaphane levels in different samples.

The results are shown in FIG. 2. The inoculated medium did not contain sulforaphane, and the level of sulforaphane could be detected as 16.76 UM after 24 h of fermentation by *B. longum* CCFM1206.

Example 3: Effect of *B. longum* CCFM1206 in Combination with Glucoraphanin-Containing Diet On Disease Symptoms in UC Mice 40 healthy male C57BL/6J mice aged 6 weeks were acclimatized for one week, and then randomly divided into 5 groups, 8 mice per group. The 5 groups were as follows: a control group, a model group, a glucoraphanin-containing diet group (BSE), a *B. longum* CCFM1206 group (CCFM1206), and a glucoraphanin-containing diet in combination with *B. longum* CCFM1206 group (BSE+CCFM1206).

The 14-day gavage intervention period was from day 8 to day 21, the dosage for each gavage was 0.2 ml/mouse, and the time for daily gavage was the same. The control and model groups were gavaged with a normal saline, the BSE group was gavaged with a 40 mg/ml solution of broccoli seed aqueous extract, the CCFM1206 group was gavaged with a $5\times10^9$ CFU/mL bacterial suspension, and the BSE+CCFM1206 group was gavaged with a mixture containing a 40 mg/ml broccoli seed aqueous extract and a $5\times10^9$ CFU/mL bacterial suspension.

Day 15 to day 21 were the last 7 days of the intervention period for ulcerative colitis modeling. DSS was added to the drinking water at a concentration of 2.5% (w/v). Mice were sacrificed on day 22, and serum, tissues and the like were collected for relevant index measurements. The experimental animals were grouped and treated as shown in Table 1.

TABLE 1

Grouping and treatment of animals

| Group | Week 1 | Week 2 | Week 3 | Day 22 |
|---|---|---|---|---|
| Control group | Acclimatization period | Gavaged with a 0.2 mL of 0.9% (w/v) normal saline | Gavaged with a 0.2 mL of 0.9% (w/v) normal saline | Mice were sacrificed |
| Model group | | Gavaged with a 0.2 mL of 0.9% (w/v) normal saline | 2.5% (w/v) DSS + gavaged with a 0.2 mL of 0.9% (w/v) normal saline | |
| BSE group | | Gavaged with a 0.2 mL solution of 40 mg/mL broccoli seed aqueous extract | 2.5% (w/v) DSS + gavaged with a 0.2 mL solution of 40 mg/mL broccoli seed aqueous extract | |
| CCFM1206 group | | Gavaged with a 0.2 mL bacterial suspension of $5\times10^9$ cfu/mL *B. longum* CCFM1206 | 2.5% (w/v) DSS + gavaged with a 0.2 mL bacterial suspension of $5\times10^9$ cfu/mL *B. longum* CCFM1206 | |
| BSE + CCFM1206 group | | Gavaged with a 0.2 mL mixture of 40 mg/mL broccoli seed aqueous extract and a bacterial suspension of $5\times10^9$ cfu/mL *B. longum* CCFM1206 | 2.5% (w/v) DSS + gavaged with a 0.2 mL mixture of 40 mg/mL broccoli seed aqueous extract and a bacterial suspension of $5\times10^9$ cfu/mL *B. longum* CCFM1206 | |

Figure 3:
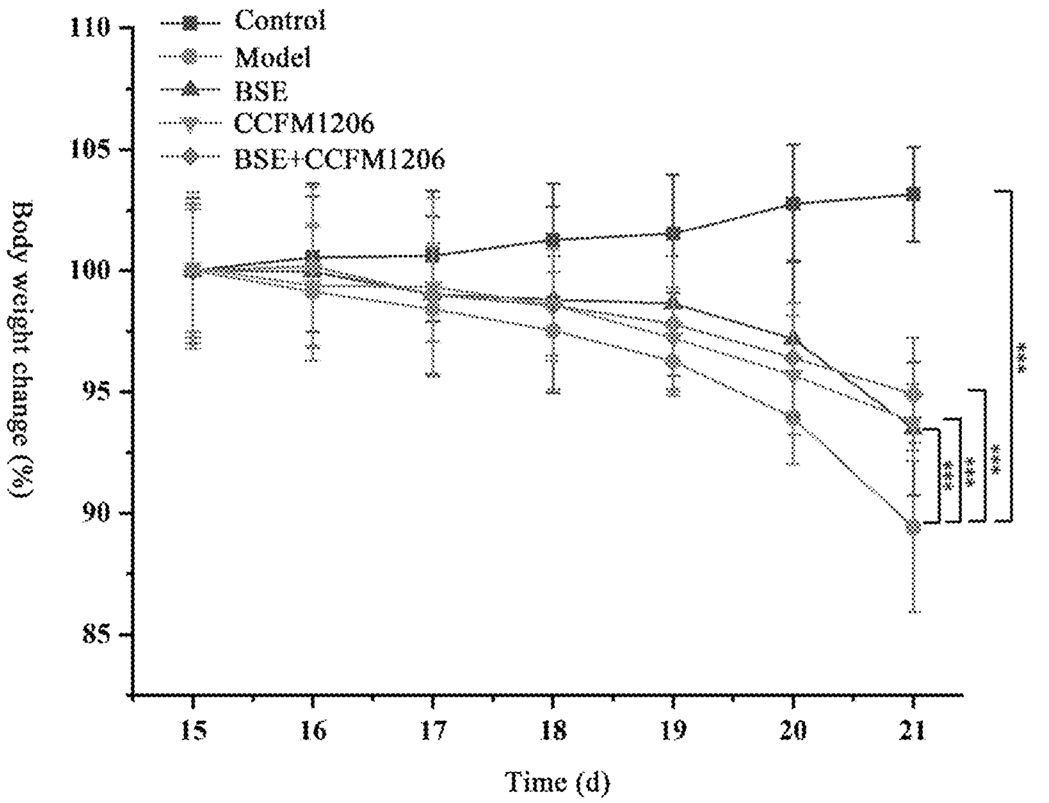
FIG. 3 is a graph showing the body weight changes of UC mice in different treatment groups.
Figure 4:
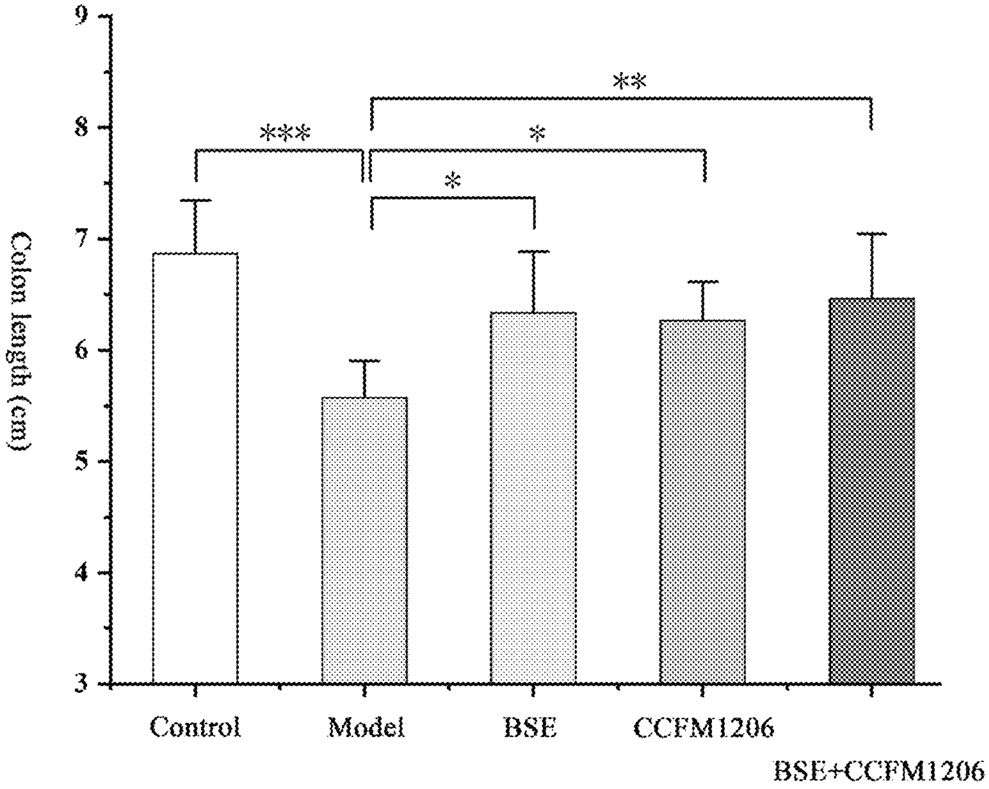
FIG. 4 is a graph showing the changes in colon length of UC mice in different treatment groups.

In the modeling period (DSS treatment period), mice were weighed regularly every day and the percentage change in body weight was calculated. After sacrificing the mice, the length of the mouse colon was measured and the average colon length was calculated for each group. The experimental results are shown in FIGS. 3 and 4. The mice in the model group showed a significant decrease in body weight from day 19 and a decrease of more than 10% in body weight on day 21. In addition, the average colon length of the mice in the model group (5.57±0.33 cm) was significantly lower than that of the control group (6.87±0.48 cm). However, weight loss and colon shortening were significantly relieved in the mice of the BSE group, the CCFM1206 group, and the BSE+CCFM1206 group. The average colon length of the mice in the BSE+CCFM1206 group (6.46±0.58 cm) was slightly higher than that of the BSE group (6.34±0.55 cm) and the CCFM1206 group (6.27±0.35 cm). These experimental results indicate that the BSE, CCFM1206, and BSE+CCFM1206 were effective in relieving the disease symptoms in mice with colitis.

Example 4: *B. longum* CCFM1206 in Combination with Glucoraphanin-Containing Diet Composition Ameliorates Colonic Mucosal Injury in UC Mice C57BL/6J mice were grouped, modeled and treated as in Example 3.

Mice were sacrificed on day 22, and mouse colon tissues were collected to make paraffin sections of mouse colon. The specific experimental steps were as follows: a 1 cm segment of distal colon 1 cm from the anus was taken and fixed with 4% paraformaldehyde for 48 h. The fixed colon tissues were rinsed with running water for 8 h, then sequentially added into 70%, 80%, and 90% ethanol solutions for dehydration, 30 min per dehydration, and then added into 95% and 100% ethanol solution, 20 min per addition. The colon samples were added in a 1:1 mixture of xylene and alcohol for 15 min, followed by xylene I and xylene II for 15 min, respectively. The colon tissues were transferred to a half-and-half mixture of xylene and paraffin for 15 min, and then added in paraffin I and paraffin II for permeation for 1 h, respectively, during which the temperature was kept at 60° C. The colon was embedded in the re-melted wax block using a Leica paraffin embedding machine, and the embedded tissues were sectioned with a tissue slicer at a thickness of 5 μm. The sections were adhered, then air-dried, and added in an oven at 62° C. for 1 h.

After the paraffin sections were made, HE staining was carried out. The specific experimental steps were as follows: paraffin sections were deparaffinized by xylene I and II for 5 min, respectively, then sequentially added into 100%, 95%, 90%, 80%, and 70% ethanol solution for 3-5 min, respectively, and finally added into distilled water for 3 min. The staining was carried out with hematoxylin for 20 s, and the unbound hematoxylin was washed away with distilled water. Then the sections were stained with eosin for 2 s, sequentially added into 95% ethanol I and II and 70% ethanol and removed quickly, then added into 80% ethanol for 50-55 s, and added into anhydrous ethanol for 2 min. Sections were added into a 1:1 mixture of xylene and alcohol for 1 min, followed by xylene I and II for 2-3 min, respectively, and then sealed with neutral gum.

Figure 5:
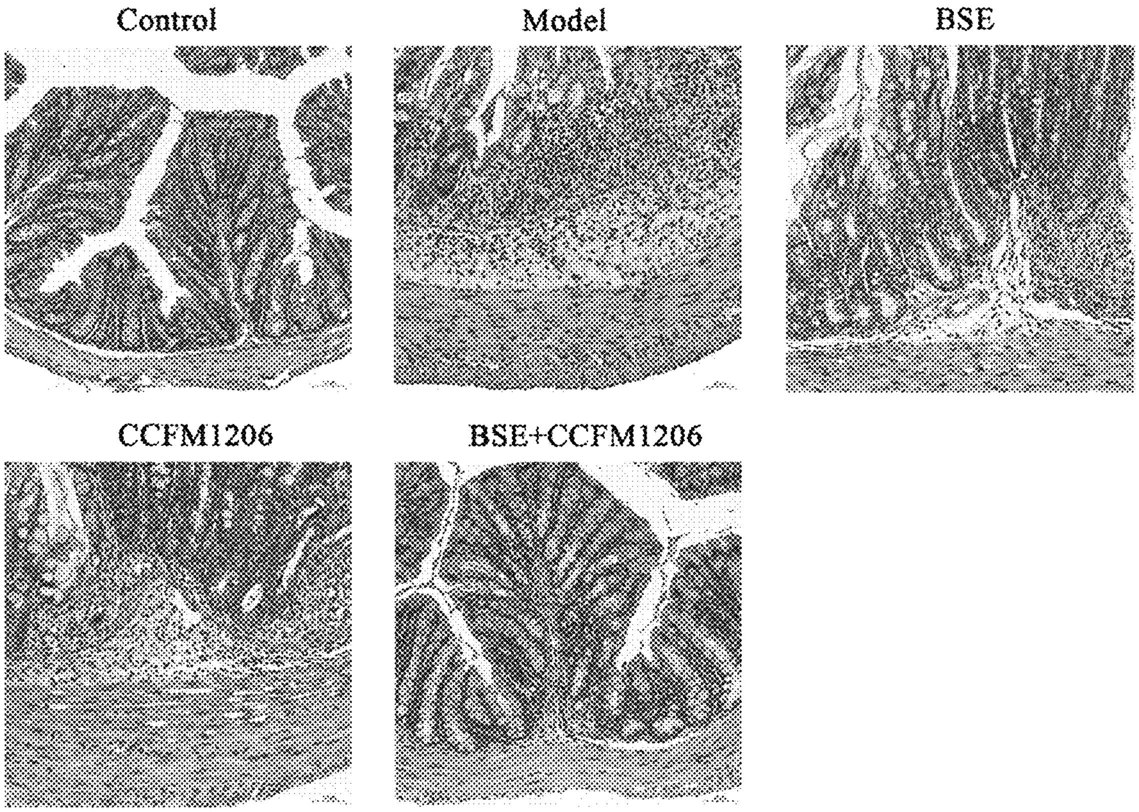
FIG. 5 is a graph showing the histomorphology (HE staining) for the colon of UC mice in different treatment groups.

The results are shown in FIG. 5. The colon of the mice in the model group showed infiltration of a large number of inflammatory cells, degeneration and necrosis of a large number of mucosal epithelial cells, a significant reduction in the number of goblet cells, disappearance of crypts, tissue edema and other pathological phenomena. Although gavage of BSE and *B. longum* CCFM1206 provided some relief of colitis, the colon tissues showed edema, infiltration of a large number of inflammatory cells as well as some reduction of goblet cells. In contrast, the colitis of mice in the BSE+CCFM1206 group was significantly ameliorated, and compared with the control group, the other structures remained basically intact except for the obvious increase in inflammatory cells. It indicates that the *B. longum* CCFM1206 in combination with glucoraphanin-containing diet can significantly ameliorate the colonic mucosal injury in UC mice, and the effect is superior to that of gavage of *B. longum* CCFM1206 or broccoli seed aqueous extract alone.

Example 5: *B. longum* CCFM1206 in Combination with Glucoraphanin-Containing Diet Composition can Significantly Reduce the Levels of Pro-Inflammatory Factors in Colitis C57BL/6J mice were grouped, modeled and treated as in Example 3.

Mice were sacrificed on day 22 and mouse colon tissue was collected. Mouse colon tissues were added to a pre-cooled PBS buffer at a ratio of 1:9 for tissue grinding and centrifuged at 12,000 g for 15 min. The supernatant was removed and the levels of TNF-α, IL-1B and IL-6 in the colon were determined according to the detection method of TNF-α, IL-1B and IL-6 ELISA kit, respectively.

Figure 6:
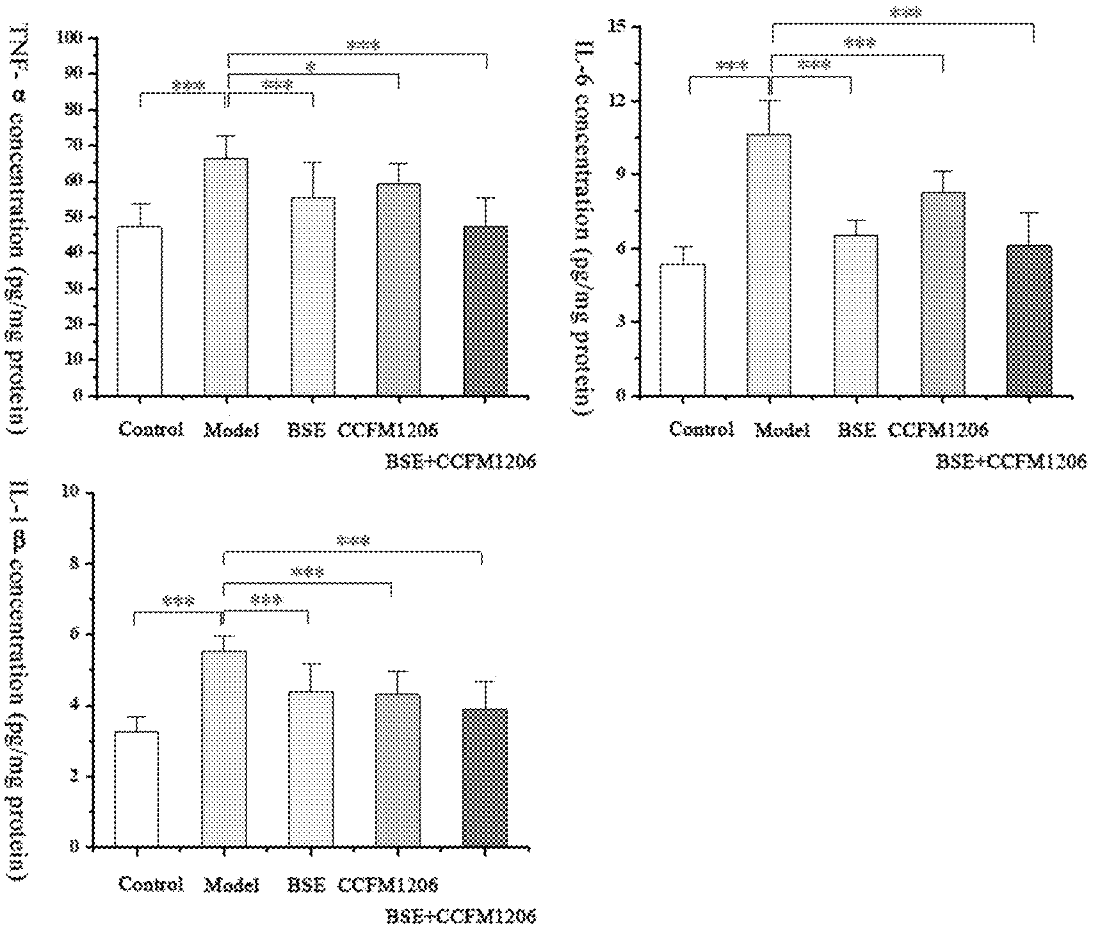
FIG. 6 is a graph showing the levels of pro-inflammatory factors in colon of UC mice in different treatment groups.

The experimental results are shown in FIG. 6. The levels of pro-inflammatory factors TNF-α, IL-6 and IL-1β were significantly increased in the colon of the mice in the model group. However, the BSE group, the CCFM1206 group, and the BSE+CCFM1206 group could reduce TNF-α from 66.53±6.12 in the model group to 55.42±9.72, 59.13±5.68, and 47.45±8.04, respectively; reduce IL-6 from 10.36±1.37 in the model group to 6.54±0.61, 8.26±0.89, and 6.10±1.35, respectively; and reduce IL-1β from 5.53±0.43 in the model group to 4.38±0.79, 4.31±0.66, and 3.91±0.76, respectively, all of which significantly reduced the levels of these inflammatory factors. However, the *B. longum* CCFM1206 in combination with broccoli seed aqueous extract composition was the most effective, with the most significant reduction in the level of inflammatory factors.

Example 6: *B. longum* CCFM1206 in Combination with Glucoraphanin-Containing Diet Composition can Enhance Intestinal Barrier Function C57BL/6J mice were grouped, modeled and treated as in Example 3.

Mice were sacrificed on day 22, and mouse colon tissues were collected to determine the transcription levels of tight junction-associated proteins Claudin-1, Occudin, and ZO-1 in the colon.

The assay was performed as follows. The primer sequences for Claudin-1, Occudin, ZO-1 and GAPDH were synthesized, and the primer information is shown in Table 3. 1 cm of colon tissue from the same part of the mouse was taken, quickly added into liquid nitrogen, frozen and stored in the refrigerator at −80° C. The frozen colon tissue was then added into a 1.5 ml enzyme-free centrifugal tube with 1 mL of TRIzol and 3 zirconium beads, homogenized thoroughly by using a tissue homogenizer, and allowed to stand at room temperature for 5 min. 0.2 mL of chloroform was added, shaken vigorously for 30 s, and allowed to stand for 10 min. Centrifugation was then performed at 12000 g for 15 min at 4° C. The upper aqueous phase was carefully pipetted into a 1.5 ml new enzyme-free centrifuge tube, and an equal volume of isopropanol was added, which were mixed by gently inverting up and down and allowed to stand at room temperature for 10 min. Centrifugation was then performed at 12000 g for 15 min at 4° C. The supernatant was discarded, 1 mL of a pre-cooled 75% ethanol was added, and the precipitate was washed by flicking. Centrifugation was performed at 12000 g for 5 min at 4° C. The supernatant was carefully aspirated and discarded, and the precipitate was blown dry on an ultra-clean bench. 50 μL of enzyme-free ultrapure water was added to dissolve the RNA. The concentration of extracted RNA was determined using a micro-spectrophotometer, and $OD_{260}/OD_{280}$ ranged from 1.9 to 2.0 was of acceptable quality. The extracted total RNA of acceptable quality was used as a template, and cDNA was synthesized according to the steps of the instruction for the reverse transcription kit. cDNA obtained by reverse transcription was subjected to qRT-PCR, and the PCR system was as follows: 5 μL of SYBR Green Supermix, 3 μL of deionized water, 0.5 μl of upstream primer (10 μmol/L), 0.5 μL of downstream primer (10 μmol/L), and 1 μl of cDNA template (100 ng/μL). qPCR program was set as follows: 94° C. for 2 min, 39 cycles (94° C. for 30 s; 61° C. for 30 s; 72° C. for 20 s). The target genes were detected by real-time PCR, and then a relative gene expression analysis was performed using GAPDH as the internal reference gene by a 2-44CT method.

TABLE 2

Primer sequences

| Gene | Forward sequence (5'-3') | Reverse sequence (5'-3') |
|---|---|---|
| Occludin | CCGGCCGCCAAGGTTC (seq ID NO: 1) | GCTGATGTCACTGGTCACCTA (seq ID NO: 2) |
| Claudin-1 | GGCTTCTCTGGGATGGATCG (seq ID NO: 3) | CCCCAGCAGGATGCCAATTA (seq ID NO: 4) |
| ZO-1 | GCCTTGAACTTTGACCTCTGC (seq ID NO: 5) | GAAATCGTGCTGATGTGCCA (seq ID NO: 6) |
| GAPDH | AGGTCGGTGTGAACGGATTTG (seq ID NO: 7) | GGGGTCGTTGATGGCAACA (seq ID NO: 8) |

Figure 7:
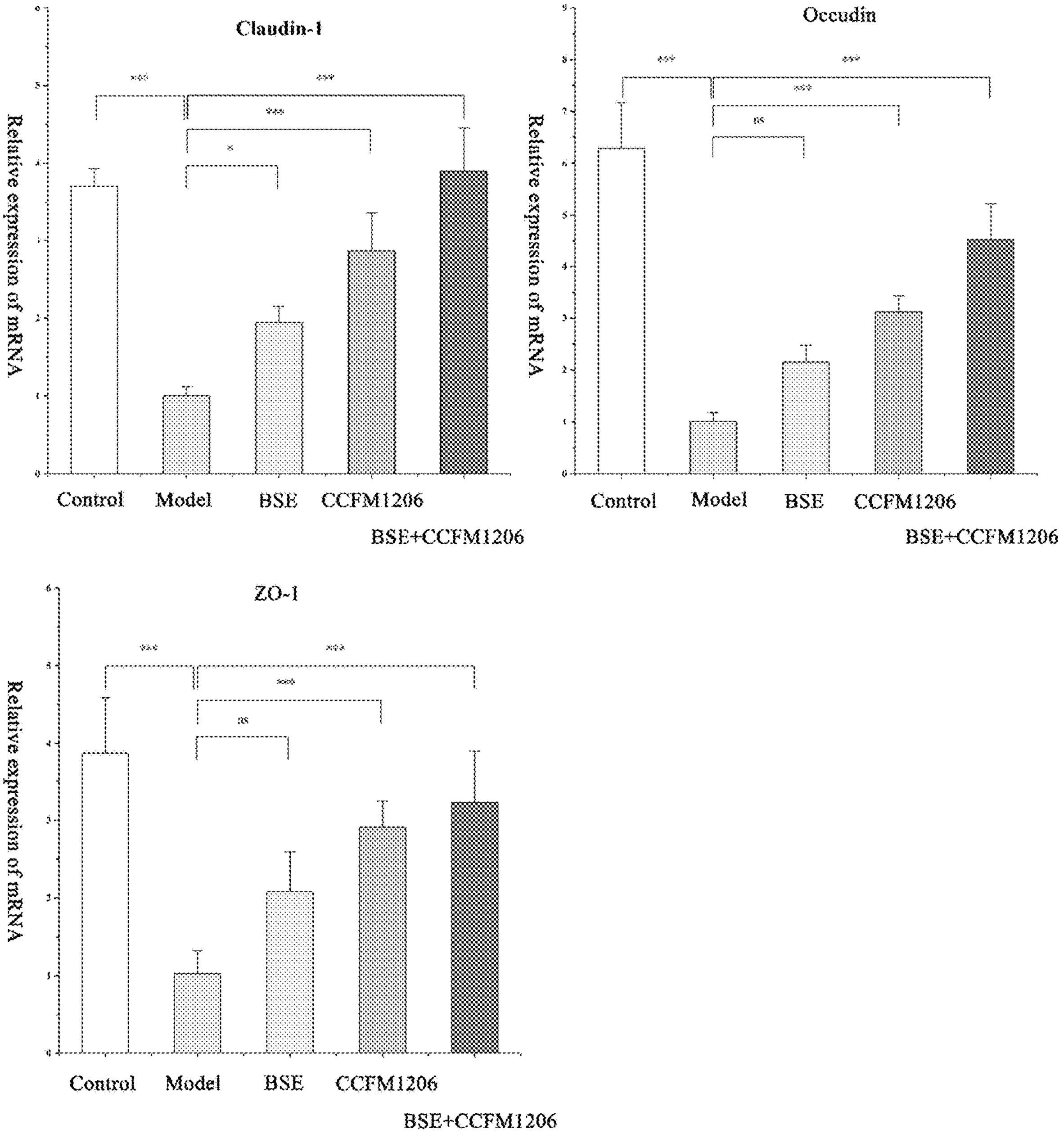
FIG. 7 is a graph showing the transcription levels of tight junction proteins in the colon of UC mice in different treatment groups.

The experimental results are shown in FIG. 7. The mRNA expression levels of three tight junction proteins, Claudin-1, Occudin, and ZO-1, were significantly decreased in the colon of mice in the model group, whereas the expression levels of these tight junction proteins were up-regulated in all of the BSE group, the CCFM1206 group, and the BSE+CCFM1206 group. Among them, the BSE group, the CCFM1206 group, and the BSE+CCFM1206 group could increase Claudin-1 from 1.00±0.11 in the model group to 1.94±0.21, 2.86±0.50, and 3.90±0.56, respectively; increase Occudin from 1.01±0.17 in the model group to 2.16±0.32, 3.12±0.31, and 4.51±0.71, respectively; and increase ZO-1 from 1.03±0.29 in the model group to 2.08±0.51, 2.91±0.34, and 3.23±0.67, respectively.

Example 7: *B. longum* CCFM1206 in Combination with Glucoraphanin-Containing Diet Composition can Reduce Spleen Index in LPS Mice 40 healthy male C57BL/6J mice aged 6 weeks were acclimatized for one week, and then randomly divided into 5 groups, 8 mice per group. The 5 groups were as follows: a control group, a model group, a glucoraphanin-containing diet group (BSE), a *B. longum* CCFM1206 group (CCFM1206), and a *B. longum* CCFM1206 in combination with glucoraphanin-containing diet composition group (BSE+CCFM1206).

The 14-day gavage intervention period was from day 8 to day 21, the dosage for each gavage was 0.2 mL/mouse, and the time for daily gavage was the same. Among which, the control and model groups were gavaged with a normal saline, the BSE group was gavaged with a 40 mg/mL solution of broccoli seed aqueous extract, the CCFM1206 group was gavaged with a $5\times10^9$ CFU/mL bacterial suspension, and the BSE+CCFM1206 group was gavaged with a mixture containing a $5\times10^9$ CFU/mL bacterial suspension and a 40 mg/ml broccoli seed aqueous extract.

The mice were injected intraperitoneally on day 22 with 0.9% normal saline in the control group and 6 mg/kg LPS in the other groups. The mice were weighed after 4 h. The mice were sacrificed, and serum, tissues and the like were collected for the determination of the relevant indexes. The experimental animal grouping and treatments are shown in Table 3.

LPS-induced systemic inflammation causes splenomegaly in mice. The spleens of mice were weighed and the spleen index was calculated as follows:

$$\text{spleen index} = \frac{\text{Spleen mass (g)}}{\text{Mouse weight (g)}} \times 100\%.$$

Figure 8:
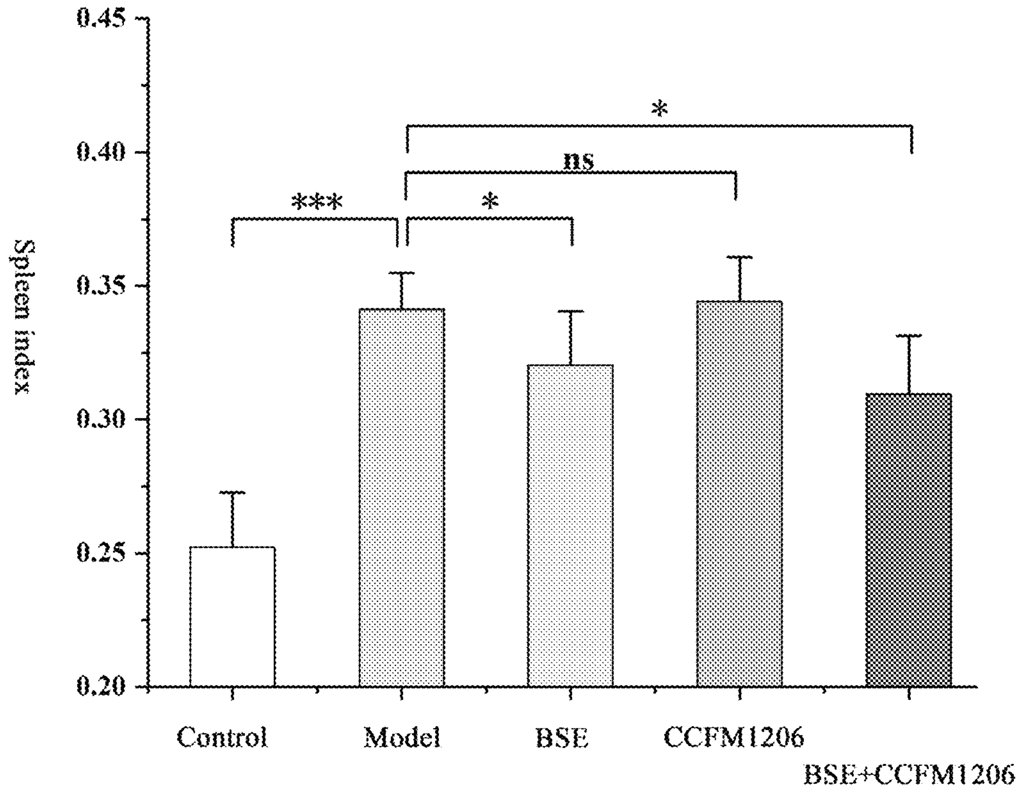
FIG. 8 is a graph showing the spleen index of LPS mice in different treatment groups.

The experimental results are shown in FIG. 8. The spleen index of the mice in the model group increased from 0.25±0.02 in the control group to 0.34±0.01, indicating that the splenomegaly due to LPS was more pronounced in the model group. However, the effect of gavage of *B. longum* CCFM1206 (0.34±0.02) on relieving the splenomegaly was not obvious, and the spleen indexes were significantly reduced to 0.32±0.02 and 0.31±0.02 by gavage of glucoraphanin-containing diet as well as *B. longum* CCFM1206 in combination with glucoraphanin-containing diet composition, respectively, compared with the control group. The effect of *B. longum* CCFM1206 in combination with glucoraphanin-containing diet composition was superior to that of gavage of glucoraphanin-containing diet alone. This indicates that the *B. longum* CCFM1206 in combination with glucoraphanin-containing diet composition can relieve splenomegaly due to inflammation.

Example 8: *B. longum* CCFM1206 in Combination with Glucoraphanin-Containing Diet Composition can Reduce the Levels of Pro-Inflammatory Factors in the Serum of LPS Mice C57BL/6J mice were grouped, modeled and treated as in Example 7.

On day 22, the plasma was collected from eyeballs in mice and centrifuged at 3500 g for 15 min, and the supernatant was taken to obtain serum. The levels of pro-inflammatory factors in serum were determined according to the detection method of TNF-α, IL-1β and IL-6 ELISA kit, respectively.

Figure 9:
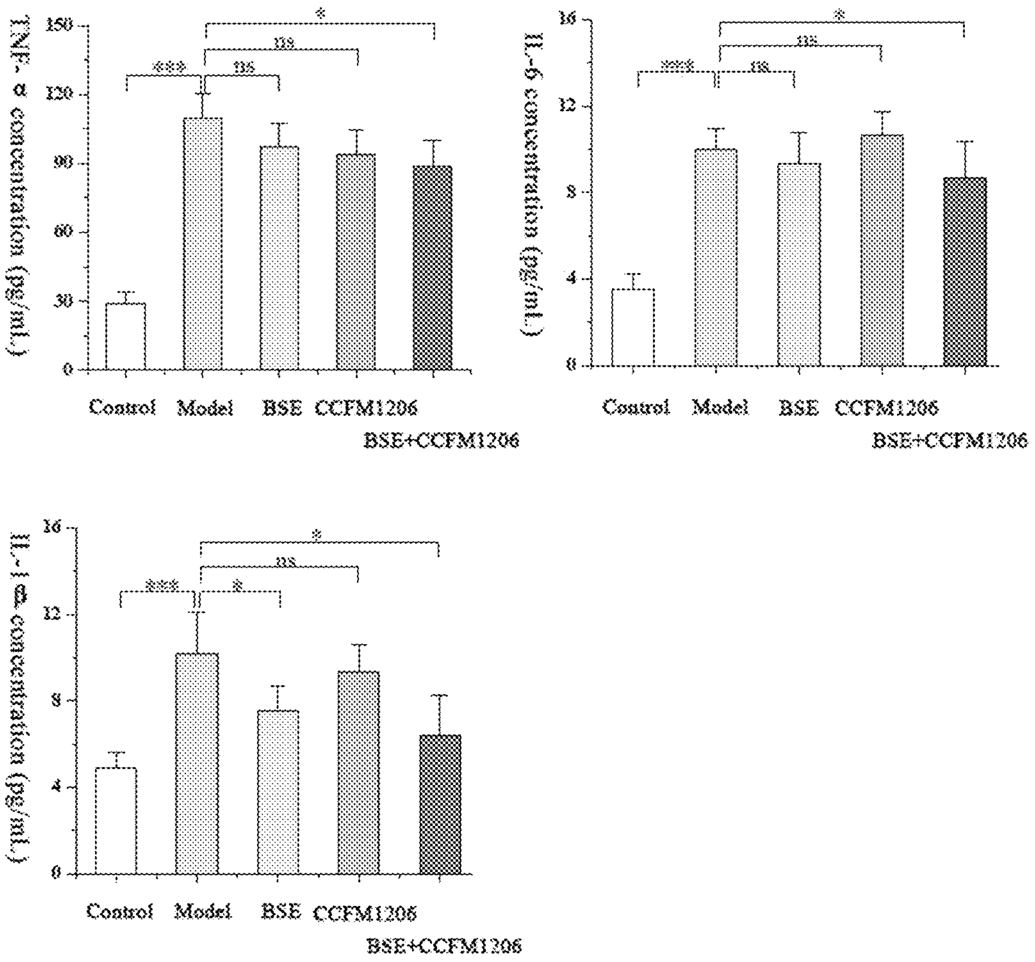
FIG. 9 is a graph showing the levels of pro-inflammatory factors in the serum of LPS mice in different treatment groups.

The experimental results are shown in FIG. 9. The serum levels of TNF-α, IL-1B, and IL-6 in mice from the model group were significantly increased to 109.39±10.71, 10.20±1.92, and 9.98±0.97, respectively, whereas the serum

TABLE 3

Grouping and treatment of animals

| Group | Week 1 | Weeks 2-3 | Day 22 | |
|---|---|---|---|---|
| Control group | Acclimatization period | Gavaged with a 0.2 mL of 0.9% (w/v) normal saline | Injected intraperitoneally with a 0.9% normal saline | After 4 h, mice were sacrificed |
| Model group | | Gavaged with a 0.2 mL of 0.9% (w/v) normal saline | Injected intraperitoneally with 6 mg/kg LPS | |
| BSE group | | Gavaged with a 0.2 mL solution of 40 mg/mL broccoli seed aqueous extract | Injected intraperitoneally with 6 mg/kg LPS | |
| CCFM1206 group | | Gavaged with a 0.2 mL bacterial suspension of $5\times10^9$ cfu/mL *B. longum* CCFM1206 | Injected intraperitoneally with 6 mg/kg LPS | |
| BSE + CCFM1206 group | | Gavaged with a 0.2 mL mixture of 40 mg/mL broccoli seed aqueous extract and a bacterial suspension of $5\times10^9$ cfu/mL *B. longum* CCFM1206 | Injected intraperitoneally with 6 mg/kg LPS | |

levels of pro-inflammatory factor TNF-α could be decreased to 97.03±10.51, 93.91±10.49, and 88.87±11.23, and the serum levels of pro-inflammatory factor IL-1β could be decreased to 7.52±1.18, 9.34±1.23, and 6.43±1.83 in mice from the BSE group, the CCFM1206 group and the BSE+CCFM1206 group, respectively. The changes in pro-inflammatory factor IL-6 were not significant in the BSE and CCFM1206 groups (9.34±1.44 and 10.63±1.09), whereas the serum levels of pro-inflammatory factor IL-6 in mice from the BSE+CCFM1206 group could be decreased to 8.68±1.64. This indicates that the *B. longum* CCFM1206 in combination with glucoraphanin-containing diet composition can relieve LPS-induced systemic inflammation in mice.

Example 9: *B. longum* CCFM1206 in Combination with Glucoraphanin-Containing Diet Composition can Reduce the Levels of Pro-Inflammatory Factors in the Liver of LPS Mice C57BL/6J mice were grouped, modeled and treated as in Example 7.

On day 22, the mice were sacrificed and then dissected to obtain the livers. Mouse liver tissues were added to a pre-cooled PBS buffer at a ratio of 1:9 for tissue grinding and centrifuged at 12,000 g for 15 min. The supernatants were removed and the levels of TNF-α, IL-6 and IL-10 in the colon were determined according to the detection method of TNF-α, IL-6 and IL-10 ELISA kit, respectively.

Figure 10:
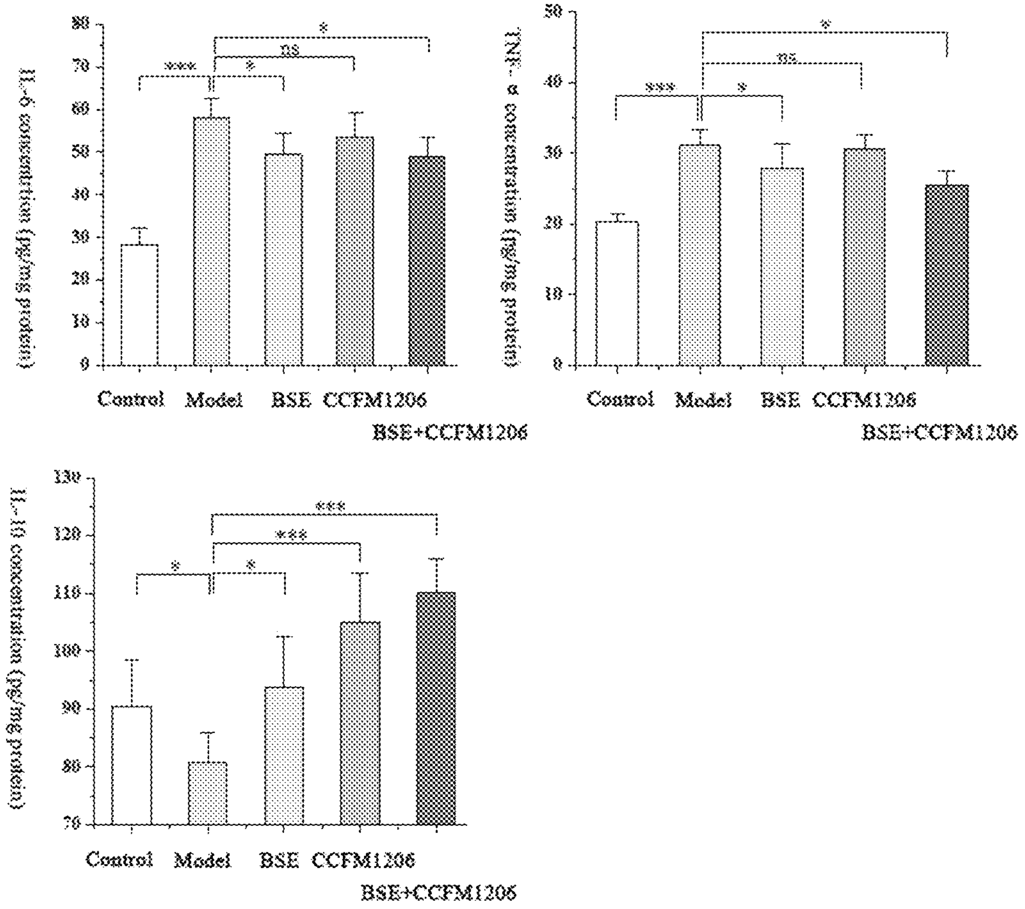
FIG. 10 is a graph showing the levels of inflammation-associated factors in the liver of LPS mice in different treatment groups.

The experimental results are shown in FIG. 10. The levels of pro-inflammatory factors TNF-α and IL-6 were significantly increased to 31.10±2.33 and 58.07±4.42, and the anti-inflammatory factor IL-10 was significantly decreased to 80.89±5.12 in the livers of the mice in the model group. Gavage of *B. longum* CCFM1206 did not significantly reduce the levels of pro-inflammatory factors TNF-α and IL-6 (30.59±1.99 and 53.62±5.59), and significantly increased the level of anti-inflammatory factor IL-10 (105.10±8.40). However, the level of pro-inflammatory factor TNF-α was significantly decreased to 27.92 and 25.51±2.03, the level of pro-inflammatory factor IL-6 was significantly decreased to 49.41±5.00 and 48.88±4.58, and the level of anti-inflammatory factor IL-10 was significantly increased to 93.82±8.76 and 110.12±5.79 in the livers of the mice gavaged with glucoraphanin-containing diet as well as *B. longum* CCFM1206 in combination with glucoraphanin-containing diet composition. This indicates that *B. longum* CCFM1206 in combination with glucoraphanin-containing diet composition can effectively relieve LPS-induced systemic inflammation in mice.

Example 10: *B. longum* CCFM1206 in Combination with Glucoraphanin-Containing Diet Composition can Increase the Levels of Short-Chain Fatty Acids in the Feces of LPS Mice C57BL/6J mice were grouped, modeled and treated as in Example 7.

The mice were sacrificed on day 22, and the contents of the mouse colon were collected, frozen and stored at −80° C. Firstly, the feces were lyophilized. 50 mg of feces was weighed, resuspended in 500 μL of saturated NaCl solution, and acidified by adding 20 μl of 10% $H_2SO_4$. 800 μL of anhydrous ether was added and shaken well. The fatty acids were extracted and then centrifuged at 13,000 g for 15 min. The upper ether phase was removed, dried by adding 0.25 g of anhydrous $Na_2SO_4$, shaken and mixed well for 30 s, and then centrifuged at 13,000 g for 10 min. The upper ether phase was removed, and the levels of short-chain fatty acids acetic acid, propionic acid, and butyric acid in the lyophilized feces of mice were determined by GC-MS.

Figure 11:
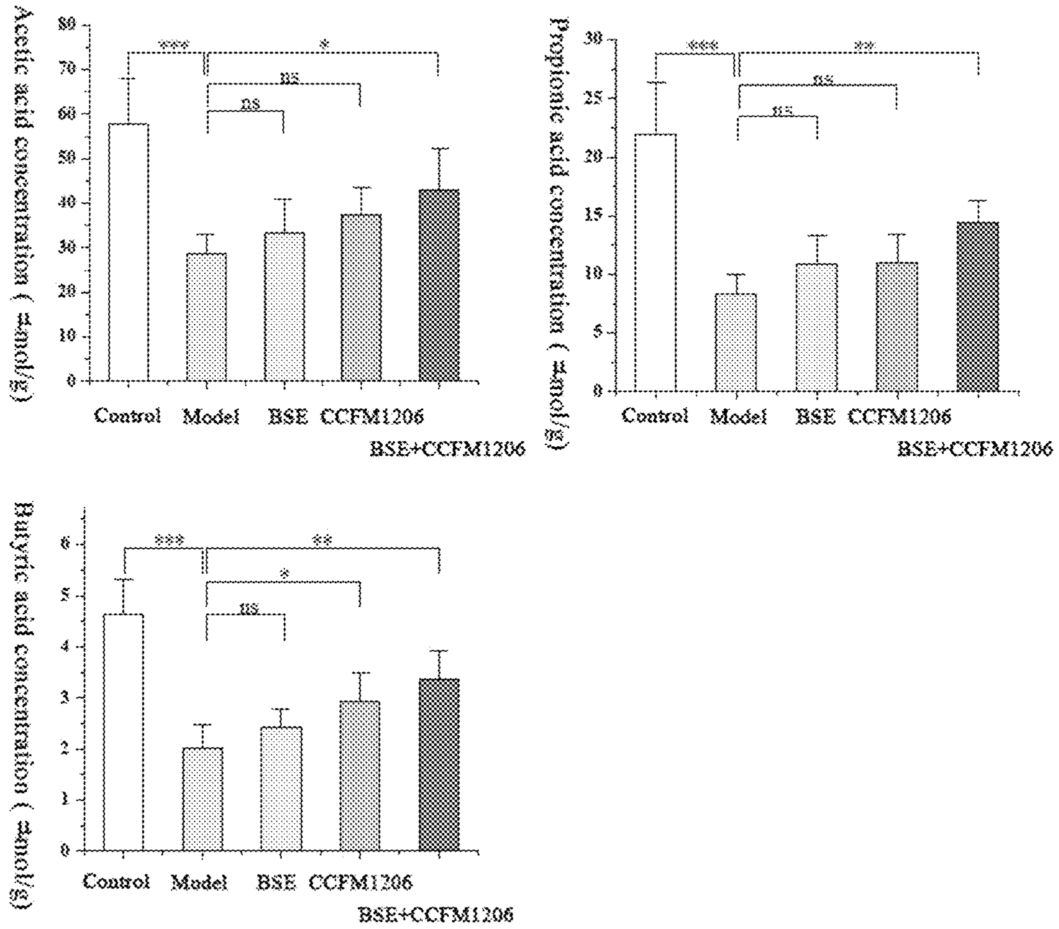
FIG. 11 is a graph showing the levels of short-chain fatty acids in the feces of LPS mice in different treatment groups.

The experimental results are shown in FIG. 11. Compared with the control group (57.68±10.17, 21.95±4.42, and 4.63±0.68), the levels of acetic acid, propionic acid, and butyric acid in the feces of mice in the model group were significantly decreased to 28.68±4.4, 8.83±1.65, and 2.03±0.45, respectively, whereas the level of acetic acid was significantly increased to 42.95±9.14, the level of propionic acid was significantly increased to 14.44±1.83, and the level of butyric acid was significantly increased to 3.35±0.56 in the feces of the mice gavaged with *B. longum* CCFM1206 in combination with glucoraphanin-containing diet composition, and the effect was superior to that of gavage of glucoraphanin-containing diet (33.37±7.42 and 10.88±2.45/2.43±0.34) or *B. longum* CCFM1206 (37.46±6.17, 10.98±2.46, and 2.91±0.58) alone.

Example 11: *B. longum* CCFM1206 in Combination with Glucoraphanin-Containing Diet Composition can Increase the Levels of Sulforaphane as Metabolized in Mice C57BL/6J mice were grouped, modeled and treated as in Examples 3 and 7.

The mice were sacrificed on day 22, and then the contents of mouse colon were collected, frozen and stored at −80° C. 100 mg of the contents were weighed and 800 μl of methanol were added to precipitate the protein. 2-3 zirconium beads were added, ground at 60 Hz for 5 min, and centrifuged at 13,000 g for 15 min (4° C.). 400 μL of supernatant was removed, evaporated to dryness, then reconstituted by adding 200 μL of methanol-water (4:1), and centrifuged at 13,000 g for 15 min (4° C.). The supernatant was passed through a 0.22 μm filter membrane and then assayed.

Figure 12:
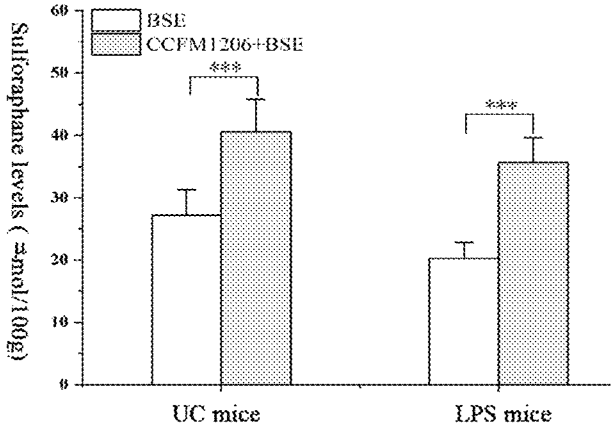
FIG. 12 is a graph showing the levels of sulforaphane in the feces of UC mice and LPS mice in different treatment groups.

The experimental results are shown in FIG. 12, no sulforaphane was detected in the contents of mice in the group without gavage of glucoraphanin-containing diet, whereas gavage of *B. longum* CCFM1206 in combination with glucoraphanin-containing diet composition significantly increased the levels of sulforaphane in the colonic contents of UC mice and LPS mice, which were 1.5 and 1.7 times higher than that of the gavage of glucoraphanin-containing diet, respectively. This means that *B. longum* CCFM1206 can increase sulforaphane production in vivo.

Example 12: *B. longum* CCFM1206 can Promote the Conversion of Dietary Glucoraphanin to Sulforaphane 24 healthy male C57BL/6J mice aged 6 weeks were acclimatized for one week, and then randomly divided into 3 groups, 8 mice per group. The 3 groups were as follows: a normal diet group, a glucoraphanin-containing diet feed group, and a glucoraphanin-containing diet feed plus gavage of *B. longum* CCFM1206 group (combination group).

The glucoraphanin-containing diet feed was a normal commercially available mouse feed additionally added with a lyophilized powder of glucoraphanin-containing vegetables or a glucoraphanin-containing vegetable extract with 0.6 mg of glucoraphanin per gram of feed. The vegetables include, but are not limited to, mixtures of vegetables such as broccoli, cabbage, and kale.

The 7-day gavage intervention period was from day 8 to day 14, the dosage for each gavage was 0.2 mL/mouse, the time for daily gavage was the same, and the feed intake in mice was about 3 g/day. Among which, the normal diet and glucoraphanin-containing diet feed groups were gavaged with a normal saline, and the combination group was gavaged with a bacterial suspension containing $5\times10^9$ CFU/mL *B. longum* CCFM1206. Mice were sacrificed on day 15, and the contents of the mouse colon were collected, frozen and stored at −80° C. 100 mg of the contents were weighed and 800 μl of methanol were added to precipitate the protein. 2-3 zirconium beads were added, ground at 60 Hz for 5 min, and centrifuged at 13,000 g for 15 min (4° C.). 400 μL of supernatant was removed, evaporated to dryness, then reconstituted by adding 200 μL of methanol-water (4:1), and centrifuged at 13,000 g for 15 min (4° C.). The supernatant was passed through a 0.22 μm filter membrane and then assayed for the levels of sulforaphane. The experimental animals were grouped and treated as shown in Table 4.

TABLE 4

Grouping and treatment of animals

| | Week 1 | Week 2 | Day 15 |
|---|---|---|---|
| Normal diet group | Acclimatization period | Given with normal mice feed, ad libitum, and gavaged 0.2 mL of 0.9% (w/v) normal saline | Collection of feces |
| Glucoraphanin-containing diet feed group | | Given with glucoraphanin-containing diet feed, ad libitum, and gavaged with 0.2 mL of 0.9% (w/v) normal saline | |
| Combination group | | Given with glucoraphanin-containing diet feed, ad libitum, and gavaged with 0.2 mL bacterial suspension of $5\times10^9$ CFU/mL *B. longum* CCFM1206 | |

Figure 13:
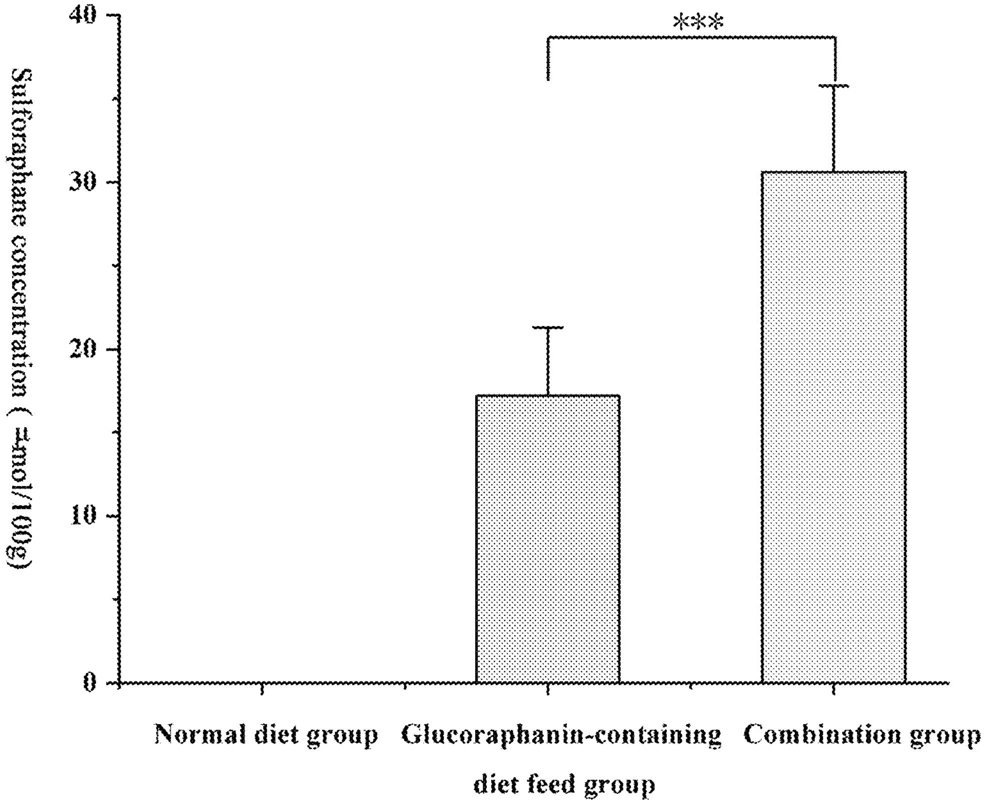
FIG. 13 is a graph showing the levels of sulforaphane in the feces of mice fed with a normal diet feed and mice fed with a glucoraphanin-containing diet feed.

The experimental results are shown in FIG. 13. No sulforaphane was detected in the contents of mice in the normal diet group, whereas sulforaphane was detected in the contents of mice given with the glucoraphanin-containing diet feed, and the levels of sulforaphane in the colonic contents of mice in the combination group under the action of *B. longum* CCFM1206 were significantly increased, which were about 1.7 times higher than that of the glucoraphanin-containing diet feed group. This indicates that *B. longum* CCFM1206 can promote the conversion of dietary glucoraphanin to sulforaphane.

Example 13: Preparation of *B. longum* CCFM1206 in Combination with Glucoraphanin-Containing Diet Composition The medium was prepared as follows: 10 g/L peptone, 10 g/L beef extract, 20 g/L glucose, 2 g/L sodium acetate, 5 g/L yeast powder, 2 g/L diammonium hydrogen citrate, 2.6 g/L $K_2HPO_4 \cdot 3H_2O$, 0.1 g/L $MgSO_4 \cdot 7H_2O$, 0.05 g/L $MnSO_4$, 1 mL/L Tween 80, and 0.5 g/L cysteine hydrochloride at pH 6.8.

Preparation of lyophilized protective agent: a protective agent containing 100 g/L skimmed milk powder, 30 mL/L glycerol, 100 g/L maltodextrin, 150 g/L trehalose, and 10 g/L sodium L-glutamate was prepared by mixing water and the ingredients of protective agent.

*B. longum* CCFM1206 was inoculated at an inoculum size of 2%-4% into the MRS medium, anaerobically incubated at 37° C. for 24 h, and centrifuged to collect the bacterium, which was rinsed with a phosphate buffer at pH=7.0-7.2 for 2-4 times and resuspended with the protective agent to reach a concentration of $10^{10}$ cfu/mL. After which, the suspension was incubated at 37° C. under an anaerobic condition for 1 h and then lyophilized to obtain the preparation of *B. longum* CCFM1206.

Optionally, the preparation is mixed with broccoli seed aqueous extract to ensure that the number of live bacteria of *B. longum* CCFM1206 in the composition is not less than $1.0\times10^6$ CFU/mL or $1.0\times10^6$ CFU/g, and the level of broccoli seed aqueous extract is not less than 200 mg/g.

Optionally, a dietary supplement may be prepared by combining the preparation of *B. longum* CCFM1206 with a vegetable or vegetable extract containing glucoraphanin. The vegetable includes, but is not limited to, one or a mixture of more than one of broccoli, cabbage, kale, and mustard.

Optionally, a functional preparation, a fermented food, or a pharmaceutical composition can also be prepared using *B. longum* CCFM1206.

Although the present disclosure has been provided as above in preferred examples, they are not intended to limit the present disclosure. Various changes and modifications can be made by any person familiar with the technology without departing from the spirit and scope according to the present disclosure, and thus the protection scope according to the present disclosure should be based on that defined in the claims.

What is claimed is:

1. A probiotic preparation comprising *Bifidobacterium longum* CCFM1206, wherein the *B. longum* CCFM1206 was deposited at Guangdong Microbial Culture Collection Center on Dec. 15, 2021 with a deposit number of GDMCC NO: 62129.

2. The probiotic preparation according to claim 1, wherein the *B. longum* CCFM1206 is present in the probiotic preparation in a level of ≥1×10$^{6}$ CFU/g or 1×10$^{6}$ CFU/mL.

3. The probiotic preparation according to claim 2, wherein the probiotic preparation further contains glucoraphanin or a broccoli seed aqueous extract.

4. A food product, nutraceutical, dietary supplement or medication containing the *B. longum* CCFM1206 according to claim 1.

5. The food product, nutraceutical, and dietary supplement according to claim 4, wherein the probiotic preparation further contains a substance containing glucoraphanin; the substance containing glucoraphanin means a vegetable or vegetable extract containing glucoraphanin; and the vegetable comprises one or a mixture of two or more of broccoli, cabbage, kale, and mustard.

6. A medication comprising the *B. longum* CCFM1206 according to claim 1, wherein the *B. longum* CCFM1206 is present in a level of ≥1×10$^{6}$ CFU/mL or 1×10$^{6}$ CFU/g.

7. A method for preventing and/or treating ulcerative colitis and systemic inflammation, wherein *B. longum* CCFM1206 is used alone or in combination with glucoraphanin as a medication.

8. The method according to claim 7, wherein amelioration of symptoms of ulcerative colitis comprises at least one of the following (1) to (4):

(1) reducing the body weight loss due to ulcerative colitis;

(2) relieving the shortening of colon length;

(3) reducing the levels of pro-inflammatory factors in colon; and (4) regulating the transcriptional levels of tight junction proteins in colon and improving the colonic barrier function.

9. The method according to claim 8, wherein the pro-inflammatory factors in colon comprise TNF-α, IL-6 and IL-1β.

10. The method according to claim 8, wherein the tight junction proteins in colon comprise Claudin-1, Occudin and ZO-1.

11. The method according to claim 7, wherein amelioration of symptoms of systemic inflammation comprises at least one of the following:

(1) relieving the splenomegaly due to inflammation;

(2) reducing the levels of pro-inflammatory factors in serum;

(3) reducing the levels of pro-inflammatory factors and increasing the levels of anti-inflammatory factors in liver tissue; and (4) increasing the levels of short-chain fatty acids in the intestines.

* * * * *

SEQUENCE LISTING

```
Sequence total quantity: 8
SEQ ID NO: 1           moltype = DNA  length = 16
FEATURE                Location/Qualifiers
```

-continued

```
source                1..16
                      mol_type = other DNA
                      organism = synthetic construct
SEQUENCE: 1
ccggccgcca aggttc                                                   16

SEQ ID NO: 2          moltype = DNA  length = 21
FEATURE               Location/Qualifiers
source                1..21
                      mol_type = other DNA
                      organism = synthetic construct
SEQUENCE: 2
gctgatgtca ctggtcacct a                                             21

SEQ ID NO: 3          moltype = DNA  length = 20
FEATURE               Location/Qualifiers
source                1..20
                      mol_type = other DNA
                      organism = synthetic construct
SEQUENCE: 3
ggcttctctg ggatggatcg                                               20

SEQ ID NO: 4          moltype = DNA  length = 20
FEATURE               Location/Qualifiers
source                1..20
                      mol_type = other DNA
                      organism = synthetic construct
SEQUENCE: 4
ccccagcagg atgccaatta                                               20

SEQ ID NO: 5          moltype = DNA  length = 21
FEATURE               Location/Qualifiers
source                1..21
                      mol_type = other DNA
                      organism = synthetic construct
SEQUENCE: 5
gccttgaact ttgacctctg c                                             21

SEQ ID NO: 6          moltype = DNA  length = 20
FEATURE               Location/Qualifiers
source                1..20
                      mol_type = other DNA
                      organism = synthetic construct
SEQUENCE: 6
gaaatcgtgc tgatgtgcca                                               20

SEQ ID NO: 7          moltype = DNA  length = 21
FEATURE               Location/Qualifiers
source                1..21
                      mol_type = other DNA
                      organism = synthetic construct
SEQUENCE: 7
aggtcggtgt gaacggattt g                                             21

SEQ ID NO: 8          moltype = DNA  length = 18
FEATURE               Location/Qualifiers
source                1..18
                      mol_type = other DNA
                      organism = synthetic construct
SEQUENCE: 8
ggggtcgttg atggcaac                                                 18
```